(12) United States Patent
Soukup

(10) Patent No.: US 8,680,297 B2
(45) Date of Patent: Mar. 25, 2014

(54) MANUFACTURING PROCESS FOR TIOTROPIUM BROMIDE

(75) Inventor: Milan Soukup, Sarasota, FL (US)

(73) Assignee: Drug Process Licensing Assoc., LLC, Dallas, TX (US)

( * ) Notice: Subject to any disclaimer, the term of this patent is extended or adjusted under 35 U.S.C. 154(b) by 322 days.

(21) Appl. No.: 13/200,975

(22) Filed: Oct. 6, 2011

(65) Prior Publication Data
US 2012/0123125 A1 May 17, 2012

(51) Int. Cl.
*C07D 409/14* (2006.01)

(52) U.S. Cl.
USPC .............................................. 549/60; 549/29

(58) Field of Classification Search
USPC ..................................................... 549/60, 29
See application file for complete search history.

(56) References Cited

U.S. PATENT DOCUMENTS

| | | | |
|---|---|---|---|
| 5,610,163 | A | 3/1997 | Banholzer et al. |
| RE39,820 | E | 9/2007 | Banholer et al. |
| 2006/0047120 | A1 | 3/2006 | Lock et al. |
| 2008/0051582 | A1 | 2/2008 | Busolli et al. |
| 2010/0099867 | A1 | 4/2010 | Busolli et al. |

Primary Examiner — Rita Desai

(57) ABSTRACT

The present invention relates to a novel manufacturing process of pharmaceutically active compound of formula I used as a long-acting anticholinergic bronchodilator. Starting from oxalic acid derivative of formula III the invention describes preparation of a novel cyclic anhydride of formula II which is very efficient precursor in the synthesis of Tiotropium bromide (compound of formula I).

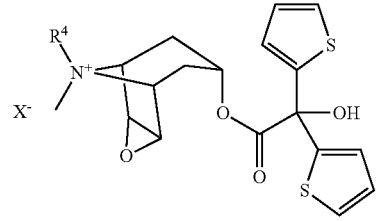

I

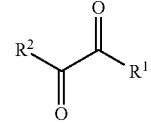

III

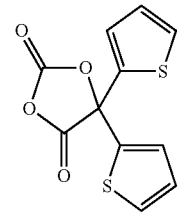

II

1 Claim, No Drawings

MANUFACTURING PROCESS FOR TIOTROPIUM BROMIDE

BACKGROUND OF THE INVENTION

Tiotropium bromide (compound of formula I, wherein $R^4$ is methyl and $X^-$ is bromide) is a long-acting anticholinergic bronchodilator used in the management of chronic obstructive pulmonary disease (COPD).

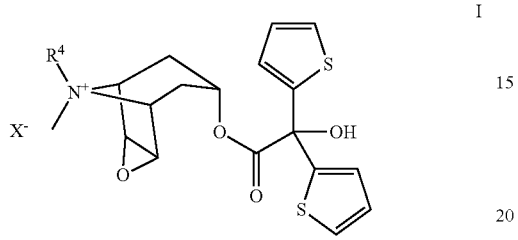

Many syntheses have been recently developed to prepare the compound of formula I: Starting from natural scopolamine hydrobromide scopine and scopine methobromide (compound of formula V) have been prepared. The second building block di(2-thienyl)glycolate is readily available via addition of 2-magnesium or lithium thiophene to oxalic acid or esters thereof. Although syntheses of both building blocks have been sufficiently resolved the coupling of both fragments, scopine or scopine methobromide with di(2-thienyl) glycolate, is still too complex comprising too many steps and low overall yield.

As disclosed in U.S. Pat. No. 5,610,163 Tiotropium bromide was synthesized via N-demethylated Tiotropium which was obtained by a reaction of methyl di(2-thienyl)glycolate and scopine using sodium metal in melt or sodium hydroxide in melt. This method is definitely not suitable for an industrial preparation. The following quarternization of N-desmethyl tiotropium was carried out in a mixture of acetonitrile and methylenechloride using methyl bromide. The scopine used for this reaction sequence was prepared first time by reduction of scopolamine using $NaBH_4$.

In U.S. Pat. No. 6,486,321 Tiotropium bromide has been prepared via tropenol derivatives involving even an additional epoxidation step.

US2006/0047120 reports another approach, direct coupling of scopine methobromide with trimethylsilyl protected sodium dithienyl glycolate prepared in situ.

US2008/0051582 discloses an improved original process using N-demethyl tiotropium in which the purity of the scopine salt should be crucial for preparative yield of the coupling reaction.

It is obvious that there is still a need for a better and more cost efficient method for coupling reaction of these two building blocks. No synthesis of Tiotropium bromide has ever been reported using a new cyclic anhydride of formula II which allows a very efficient coupling of both building blocks in high preparative yield and high purity.

SUMMARY OF THE INVENTION

The present invention discloses a novel technical process for the manufacture of Tiotropium bromide of formula I from inexpensive, readily available cyclic anhydride of formula II as shown in Scheme 1:

Scheme 1

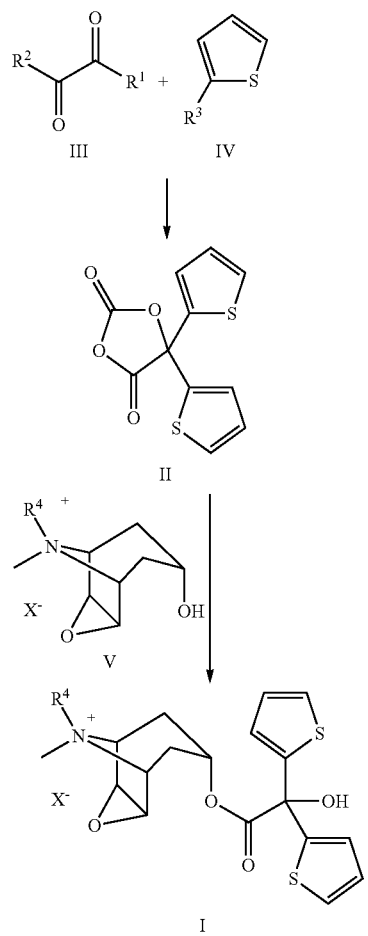

Treatment of oxalic acid derivative of formula III with an organometallic reagent of formula IV provides in situ tert.-alkoholate which undergoes readily reaction with phosgene like reagent providing cyclic anhydride of formula II which can readily converted with compound of formula V directly into Tiotropium compound of formula I.

DETAILED DESCRIPTION OF THE INVENTION

The present invention claims a process according to Scheme 1 for preparation of a compound of formula I,

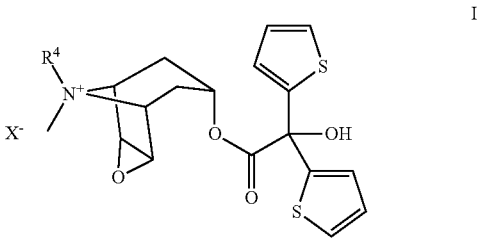

wherein $R^4$ is hydrogen, methyl or void and $X^-$ is anion with a single negative charge, preferably anion selected from among of inorganic or organic acid as chloride, bromide, iodide, methanesulphonate, trifluoromethanesulphonate, or void and nitrogen is then in the form as tert.-amine without a positive charge,
comprising following steps:
a) reaction of the compound of formula III,

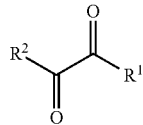

wherein $R^1$ is hydroxy, alkoxy, aryloxy, alkylaryloxy, arylalkoxy, preferably methoxy and ethoxy, and
$R^2$ is hydroxy or alkoxy, aryloxy, alkylaryloxy, arylalkoxy, preferably methoxy, ethoxy, or —O⁻Me⁺, wherein Me⁺ is alkali or earth alkali metal cation, preferably Li, Na, K, Mg, Ca or Ba,
with a compound of formula IV

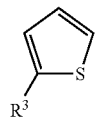

wherein $R^3$ is a metal containing group especially an alkali or earth alkali metallic radical, as lithium, sodium, potassium or a group of formula Mg-halogen (Grignard reagent), —Znhalogen, -Cer(halogen)$_2$ or boronic acid as —B(OH)$_2$, but preferably —Li or —MgBr or -Mgate complex, in inert organic solvent, preferably THF,
followed by reaction with a reagent Lvg-C(=O)-Lvg, wherein Lvg is a suitable leaving group, preferably reagent such as phosgene, (ClCOCl), di- or tri-phosgene (ClC(=O)OCCl$_3$ or Cl$_3$COC(=O)OCCl$_3$) or N,N-carbonyl diimidazole or alkyl- or aryl-chloroformate such as ClC(=O)Oalkyl, ClC(=O)Oaryl, Cl(=O)COalkylaryl, ClC(=O)Oarylalkyl,
providing a compound of formula II

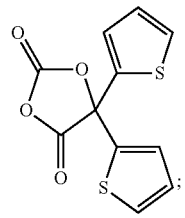

b) reaction of compound of formula II with a compound of formula V,

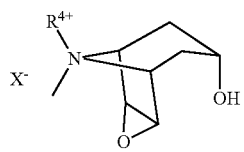

wherein $R^{4+}$ and $X^-$ are the same as defined for compound of formula I.
Compound of formula III can be any oxalic acid derivative, preferably oxalic acid itself or oxalic acid diester with lower alkyl, aryl or arylalkyl ester group, or a half ester containing lower alkyl or aryl or arylalkyl ester group, wherein the carboxylic acid function could be either a free acid or a salt thereof with alkali or earth alkali metal cation or an ammonium salt as e.g. tetraalkyl ammonium salt. In order to avoid an excess of the organo metallic reagent of formula IV, it is preferable to use a half ester sodium or lithium salt of formula III. The most preferred form is half methyl ester mono lithium or sodium salt of oxalic acid.

In the preferred embodiment of the invention the compound of formula IV, wherein $R^3$ is a metal containing group, especially an alkali or earth alkali metallic radical, such as lithium, sodium, potassium or a group of formula Mg-halogen, —Znhalogen, -Cer(halogen)$_2$ or boronic acid as —B(OH)$_2$, but preferably —Li or —MgBr or -Mgate complex, is prepared from corresponding aromatic halide (a compound of formula IV, wherein $R^3$ is a halide, preferably bromide) and it is used in situ in an inert solvent, such as THF, at a temperature range of −78° C. to 70° C.

The addition of the compound of formula IV to a compound of formula II can be carried out in an inert solvent, such as THF or dialkyl ether or toluene, at a temperature range of −78° C. to 70° C. similar as already reported in US2010/0099867, US2006/0047120, US2008/0051582 or Acta Chim. Scand. 1970, 24, 1590.

In situ formed tert.-alkoholate from di(2-thienyl)glycolate is then used directly without isolation in the following reaction with phosgene: As phosgene like reagent Lvg-C(=O)-Lvg can be used, wherein Lvg is a suitable leaving group. Preferably reagent as phosgene, (ClCOCl), di- or tri-phosgene (ClC(=O)OCCl$_3$ or Cl$_3$COC(=O)OCCl$_3$) or N,N-carbonyl diimidazole or even alkyl- or aryl-chloroformate such as ClC(=O)Oalkyl, ClC(=O)Oaryl, Cl(=O)COalkylaryl, ClC(=O)Oarylalkyl can be used. Cyclic anhydrides have been already prepared as reported e.g. in Heterocycles 1989, 29, 975 or in JACS 1993, 115, 6078 or JOC 1993, 58, 3789, or in Organic Proc. Res. & Develop. 2010, 14, 921.

Since the cyclic anhydride of formula II hydrolyzes readily in water a non aqueous work up is preferred process for the isolation. Compound of formula II is either used in situ followed by addition of the compound of formula V or it can be first isolated by simple filtration of the reaction mixture and evaporation of the solvent from the filtrate. Then the crude compound of formula II can be subjected reaction with compound of formula V in a separate step. As preferred solvents any inert solvents can be used, preferably ether, acetonitrile, DMF or even aromatic hydrocarbons as toluene are beneficial at a temperature range of −20° C. to 90° C. DMAP or other tert.-amines are beneficial for reaction of the compound of formula II with compound of formula V. During the coupling reaction carbon dioxide is the only side product which is liberated from the reaction mixture and consequently, just simple crystallization of the reaction mixture provides pure Tiotropium bromide of formula I.

An example is provided to illustrate particular aspects of the disclosure and does not limit the scope of the present invention as defined by the claims.

EXAMPLES

Determination of purity was carried out with HPLC using columns as Chiralcel OJ-H, Chiralpak AS-H or Chiralpak AD-H from Daicel Chem. Ind. If not mentioned otherwise, all evaporations are performed under reduced pressure, preferably between 5-50 Torr, in some case even under high vacuum. The structure of final products, intermediates and starting materials is confirmed by standard analytical methods, e.g. spectroscopic characteristics as MS or NMR or IR. Abbreviations used are those conventional in the art.

Example

Preparation of Tiotropium Bromide (I) from Oxalic Acid of Formula IIIa

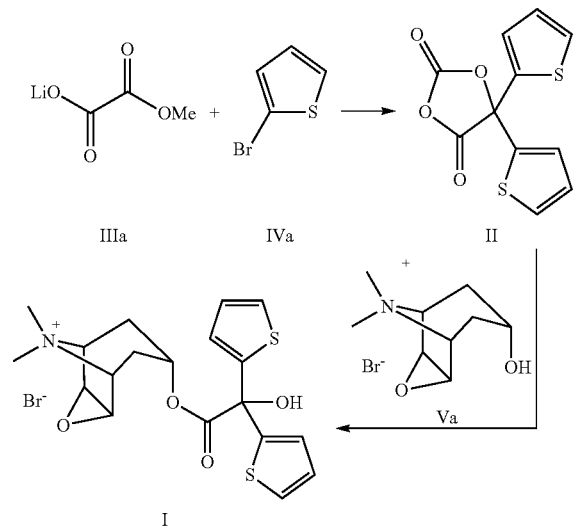

Step IIIa and IVa→II:

In inert atmosphere to a suspension of Li oxalate half methyl ester (IIIa, 110 g) in THF (900 ml) cooled to −20° C. under good stirring 2-Mg-thiophene solution (IVa) as prepared below, was slowly added that the reaction temperature remained at maximum 5-10° C. After addition the solution was stirred at the same temperature for ca. 3 hrs.

After the reaction was completed (monitored by GC or TLC) to this stirred reaction mixture diphosgene (200 g), diluted in THF (200 ml), was slowly added in ca. 30 min at controlled temperature of 10-20° C. After addition the reaction mixture was slowly warmed up to rt and stirred for ca. 10 hrs. The completion of the reaction was monitored with TLC or HPLC. If some unreacted tert.-alkoholate should still be present, further addition of diphosgene shall be necessary for the completion. After addition of activated charcoal (25 g) and hexane (2000 ml) the reaction mixture was filtered, the filtrate concentrated under reduced pressure (2-5 Torr) and finally dried on high vacuum to give yellow viscous oil of crude compound II (240 g) which solidified slowly and was used directly in the next step.

Step II→I:

Scopine methobromide Va (235 g), dimethyl aminopyridine (DMPA, 900 mg) and DMF (5 ml) were suspended in acetonitrile (1500 ml) and to this slurry anhydride of formula II (265 g), dissolved in acetonitrile (500 ml), was slowly added within ca. 1 hr. After addition the reaction mixture was heated under reflux for ca. 4 hrs until the reaction was completed. The progress of the reaction was monitored with HPLC or TLC. For work up the reaction mixture was slightly concentrated under vacuum to a volume of ca. 300 ml, then stirred over night at rt for crystallization. The product was filtered and washed twice with acetonitrile (2×80 ml), dried under high vacuum to give Tiotropium bromide I as colorless crystals: 405 g (85% yield, purity HPLC: 99.8%). Analysis calculated for $C_{19}H_{22}BrS_2NO_4$: C, 48.31; H, 4.69; Br, 16.91; S, 13.58; N, 2.96; O, 13.55. Found: C, 48.32; H, 4.61; Br 16.98; S, 13.55; N, 3.02; O, 13.61. The analytical data of I have been identical with published as in U.S. RE39,820 E, Example 4.

Preparation of 2-thienyl magnesium bromide (IVa)

In another flask in inert atmosphere under stirring magnesium (50 g) in THF (1000 ml) has been suspended. To this slurry under stirring initially 1,2-dibromo butane (1 ml) and then 2-bromo thiophene (330 g), in THF (100 ml), were slowly added that the reaction temperature remained at ca. 50-55° C. (cooling!). After addition the reaction mixture was heated to 65° C. for ca. 2 hrs, then cooled to rt and used as described in the procedure above.

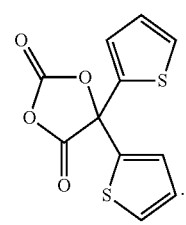

The invention claimed is:
1. A compound of formula II